US006984387B1

(12) United States Patent
Correa et al.

(10) Patent No.: US 6,984,387 B1
(45) Date of Patent: Jan. 10, 2006

(54) IMMUNOGENIC PEPTIDES OF FOOT-AND-MOUTH DISEASE VIRUSES

(75) Inventors: Roberto Correa, Leverkusen (DE); Hans-Robert Hehnen, Siegburg (DE); Eberhard Pfaff, Schwaigern (DE); Armin Saalmüller, Reutlingen (DE); Thomas Pauly, Neu Isenburg (DE); Bettina Höhlich, Tübingen (DE); Bernadette Glatthaar-Saalmüller, Reutlingen (DE); Karl-Heinz Wiesmüller, Tübingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/254,966

(22) PCT Filed: Sep. 8, 1997

(86) PCT No.: PCT/EP97/04866

§ 371 (c)(1),
(2), (4) Date: Mar. 16, 1999

(87) PCT Pub. No.: WO98/12333

PCT Pub. Date: Mar. 26, 1998

(30) Foreign Application Priority Data

Sep. 18, 1996 (DE) ............................... 196 38 044

(51) Int. Cl.
*A61K 39/125* (2006.01)
(52) U.S. Cl. .............................. 424/216.1; 424/186.1; 530/300; 530/327
(58) Field of Classification Search ............ 424/130.1, 424/184.1; 435/5, 7.1, 7.92, 68.1, 69.3; 530/300, 530/326
See application file for complete search history.

(56) References Cited

U.S. PATENT DOCUMENTS 4,605,512 A * 8/1986 Schaller et al. ........ 260/112.005
5,639,601 A * 6/1997 Saeki et al. .................. 435/5
6,048,538 A 4/2000 Yi Wang et al. ......... 424/216.1

OTHER PUBLICATIONS

Zamorano et al., "A 10-amino-acid linear sequence of VP1 of foot and mouth disease viruses containing B- and T-Cell epitopes induces protection in mice." Virology vol. 212 (1995), p. 614-621.*
Rodriguez et al., "Immunogenicity of non-structural proteins of foot and mouth disease virus: differences beween infected and vaccinated swine." Archives of Virology vol. 136 (1994), p. 123-131.*
Lubroth et al., "Absence of protein 2c from clarified foot and mouth disease virus vaccines provides the basis for distinguishing convalescent from vaccinated animals." Vaccine vol. 14 (1996), p. 410-427.*
Morgan et al., "Protection of cattle and swine against foot and mouth disease, using biosynthetic peptide vaccines." American Journal of Vetrinary Research vol. 51 (1990), p. 40-45.*
Francis et al., "Immune response to uncoupled peptides of foot and mouth disease virus." Immunology vol. 61 (1987), p. 1-6.*
Zamorano et al., "Recognition of B and T cell epitopes by cattle immunized with a synthetic peptide containing the major immunogenic site of VP1 FMDV 01 Campos." Virology vol. 201 (1994) p. 383-387.*
Van Lierop et al. The influence of MHC polymorphysim on the selection of T-cell determinants of FMDV in cattle. Immunology. vol. 84 (1995) pp. 79-85.*
Gene Bank Accession #P03308.*
J. Immunol., vol. 138, Mar. 15, 1987, Saalmüller et al, pp. 1852-1857, Monoclonal Antibodies Reactive With Swine Lymphocytes II. Detection of an Antigen on Resting T Cells Down-Regulated after Activation.
Immunobiol., vol. 190, (month unavailable) 1994, Saalmüller et al, pp. 23-34, Major Histocompatibility Antigen Class II Expressing Resting Porcine T Lymphocytes are Potent Antigen-Presenting Cells in Mixed Leukocyte Culture.
Immunology, vol. 81, (month unavailable) 1994, Saalmüller et al, pp. 578-583, Discrimination between two subsets of porcine CD8+ cytolytic T lymphocytes by the expression of CD5 antigen.
Journal of Gen. Virology, vol. 76, (month unavailable) 1995, pp. 3039-3049, Pauly et al Classical swine fever virus-specific cytotoxic T lymphocytes and identification of a T cell epitope.
Cell. Immunol., vol. 168, (month unavailable) 1996, Summerfield et al, Functional Characterization Of Porcine CD4+CD8+ Extrathymic T Lymphocytes, pp. 291-296.
Immunology, vol. 88, (month unavailable) 1996, pp. 238-246, Pauly et al, Differentiation between MHC-restricted and non-MHC restricted porcine cytolytic T lymphocytes.

* cited by examiner

*Primary Examiner*—Ulrike Winkler
(74) *Attorney, Agent, or Firm*—Susan M. Pellegrino

(57) ABSTRACT

The present invention relates to FMDC vaccine based on peptides having a sequence of at least 8 amino acids, which corresponds to a partial sequence of the non-structural protein region of FMDV, which was selected by immunoreactivity with FMDV-specific antibodies or by immunoreactivity with FMDV-specific T lymphocytes, and to their production and their use.

1 Claim, No Drawings

IMMUNOGENIC PEPTIDES OF FOOT-AND-MOUTH DISEASE VIRUSES

The present invention relates to immunogenic peptides having at least 8 amino acids, which occur in non-structural regions of the foot and mouth disease virus (FMDV).

Foot-and-mouth disease (FMD) is an acute infectious disease which occurs in the most important milk and meat producers—cattle, pigs, goats and sheep.

The cause of the disease is a picornavirus, the foot-and-mouth disease virus (FMDV). This is an RNA virus having a single-stranded RNA 8.5 kb long with a plus strand polarity, which can occur in various serotypes having numerous subtypes. Animals which have recovered from infection with one serotype remain totally susceptible to infection with another serotype.

Primary replication of the virus, after infection via the airways, takes place in the pharynx. Neighbouring lymph nodes are then infected and the FMDV crosses into the blood. Via the blood, the virus spreads into the various organs and tissues. Clinical symptoms occur 2–14 days after infection, depending on the virus dose, strain and route of infection. In less serious cases, infection is overcome after 14 days. FMDV infection only rarely has a fatal outcome in older animals, but has a considerable effect on their productivity, growth and well-being. Moreover, it is possible for the healthy animals to excrete the FMDV in spite of high antibody titers and thus infect other animals. Vaccinated animals which were exposed to the infectious virus are also problematic. These animals can also remain persistently infected without showing clinical symptoms. These animals, which are admittedly healthy but despite this carry FMDV, are described as "carriers" and are a serious danger in the further spread of FMDV. Isolation of the virus from pigs is possible up to one month after infection (Van Bekkum; 1973), and in cattle even more than several years (Hedger, 1970).

The coat of the virus particle consists of 60 copies each of the 4 structural proteins 1A–1D (Rueckert, 1990) which enclose the single-stranded RNA. The capsid is not coated and has an icosahedral shape. The proteins 1B–1D lie partly on the surface, while the protein 1A (P1A) lies in the interior of the capsid.

The proteins 1A–1D encoded in the N-terminal part of the genome are structural proteins and form the icosahedral capsid. The non-structural proteins 2A–2C and 3A are C-terminal encoded and responsible for virus replication.

The control of FMD is made difficult by the easy transmissibility of the virus, its ability infect many animal species and its multiple antigenic forms.

Vaccination against FMD was carried out in Germany up to 1992 using a trivalent killed vaccine for the subtypes O, A and C. These vaccines consisting of inactivated viruses, however, are thermally unstable and do not guarantee any long-lasting immunity (Terpstra et al., 1989). The danger which emanates from the vaccines consists above all in the presence of uninactivated viruses in the killed vaccine and the release of virus from the respective vaccine production sites (Beck et al., 1987).

In the European Union (EU), trade restrictions apply to animals in which antibodies against FMDV can be detected. This applies both to animals which have possibly survived infection, and to animals immunized using a conventional killed vaccine.

For this reason, there have been increased attempts since then to develop better vaccines against FMDV. It would be desirable to get hold of vaccines which are distinguished by longer shelf life, better activity and greater safety. An additional advantage would be vaccines or methods which make it possible to differentiate between vaccinated and infected animals.

Three things particularly have to be taken into account in the development of vaccines having specific epitopes:

1. Polymorphism of proteins of the pathogen occurs especially in the protein sections involved in the immune response. RNA viruses especially ("quasi-species"), contain regions of extremely high sequence variability.
2. Especially in the case of the T-cell immune response, there is a high variability of single individuals of the host species. As a rule, a T-helper cell recognizes a specific antigenic peptide only in combination with a specific MHC-II molecule (Schwartz, 1985). Each individual expresses its own set of MHC molecules, which are encoded by genes having high allelic variation (MHC polymorphism). A T-cell response to peptides can therefore be individually different.
3. The T-cell fractions exhibit very heterogeneous effector mechanisms which nevertheless as a rule correlate with the MHC restriction (Mosmann et al., 1989). For FMDV in cattle, it was hitherto only possible to demonstrate MHC-II-restricted T-helper functions (Glass et al., 1989; Glass et al., 1990; Glass et al., 1992; Collen et al., 1991).

For the preparation of peptide vaccines, the immunogenic regions of the pathogen must first be known, that is the sites of a pathogen which are recognized by the immune system of the natural host species, i.e. by the B or the T lymphocytes of cattle and pigs. There was hitherto no knowledge about these.

It has now been found that FMDV vaccines can be prepared based on peptides having a sequence of at least 8 amino acids, which corresponds to a partial sequence of the non-structural protein region of FMDV, which was selected by immunoreactivity with FMDV-specific antibodies or by immunoreactivity with FMDV-specific T lymphocytes.

Such peptides preferably consist of 8–35 amino acids, particularly preferably of 8–25 amino acids, very particularly preferably of 8–15 amino acids.

For the preparation of an FMDV vaccine for pigs, such peptides must correspond to parts of regions on the genome of FMDV which code for the proteins L/L', 1A, 1B, 1C, 2B, 2C, 3A, 3B, 3C and 3D.

For the preparation of an FMDV vaccine for cattle, such peptides must correspond to parts of regions on the genome of FMDV which code for the proteins 1D, 2B, 2C, 3A and 3B.

Peptides are therefore particularly preferred which correspond to parts of regions on the genome of FMDV which code for the proteins 2A, 2B, 2C, 3A, 3B, 3C and 3D.

The peptides mentioned in the sequence protocol may be mentioned specifically here.

Particular emphasis may be given to the peptides mentioned in the sequence protocol having the ID numbers: 6, 8, 10, 12, 15, 16, 17, 18, 19, 20, 21, 23, 24, 25, 26, 27, 28, 29, 30, 31, 32, 34, 35, 36, 37, 38, 39, 43, 44, 45, 48.

Particular emphasis may additionally be given to the peptides having the ID numbers 12, 13, 14, 22, 33, 37, 40, 41, 42, 45, 46, 47.

Very particular emphasis may be given to the peptides having the ID numbers: 12, 37, 40, 42, 45.47, 48.

Products which include these peptides can be used both for immunization for protection against the foot-and-mouth disease virus, and also for the detection of an FMDV infection. i.e. for diagnostic purposes.

As already mentioned, the peptides according to the invention correspond in subregions to the non-structural proteins of FMDV. These regions are determined by immunoreactivity with FMD-specific antibodies or by immunoreactivity with FMDV-specific T lymphocytes.

Immunoreactivity in this connection is understood as meaning the reactivity with FMDV-specific antibodies. The detection of a reaction is in this case carried out by means of an interaction of the FMDV-specific antibodies with the peptides bound to a solid phase via an enzyme immunoassay which includes a colour reaction. A further possibility of detecting the reactivity consists in the detection of the competition of the binding of the FMDV-specific antibodies to recombinant viral proteins by the peptides concerned.

Immunoreactivity is also understood as meaning the reactivity of the peptides with lymphocytes which were obtained from FMDV-infected/vaccinated animals. After co-incubation with the peptides concerned, these lymphocytes are able to exhibit specific reactions: a) increased peptide concentration-dependent growth (a peptide antigen-specific proliferation); b) a peptide-specific increased production of specific substances (cytokines, e.g. interleukin-2); c) and also differentiation to give virus-specific cytolytic T lymphocytes which are able to recognize the peptides concerned in association with molecules which are encoded by the major histocompatibility complex (MHC), and to lyse cells which carry the peptides concerned on the surface.

FMD-specific antibodies are antibodies which are formed in the animal after vaccination or after infection with FMDV and are able to recognize certain structures of FMDV and to bind to these structures. They can be demonstrated ex vivo, and in vitro with the aid of a virus-specific enzyme immunoassay. The FMDV-specific antibodies in this case recognize either the entire virus, certain viral proteins or protein fragments in the form of peptides which are encoded by virus-specific sequences.

FMD-specific T lymphocytes can be obtained by isolating mononuclear cells from the blood of FMDV-infected or vaccinated animals.

In the following, a general survey of the possible methods for the obtainment of the peptides according to the invention is given. These methods are only intended to illustrate the invention, but not to restrict it in any way.

For the obtainment of mononuclear cells from the blood (peripheral blood mononuclear cells, PBMC) of pigs, heparinized blood (0.1 mg of heparin per ml of blood) is diluted with PBS in the ratio 1:2. 30 ml each of this are layered at room temperature onto 15 ml of Ficoll-Hypaque (1.077 g/ml layered in 50 ml tubes). After centrifugation for 25 min at 1,100 g, the mononuclear leucocytes can be carefully pipetted off from the inter phase between serum and Ficoll. The cells isolated in this way are washed and pelleted (in each case 10 min, 750 g) once with PBS and twice with 20 ml each of lymphocyte culture medium/10% FCS in 50 ml tubes.

Concentration of T Lymphocytes by Means of Nylon Wool Columns

This method of concentration of T lymphocytes is based on the physical adherence of lymphocytes and some of the monocytes to nylon wool. For this purpose, the nylon wool is boiled three times in distilled water, stuffed loosely up to the 5 ml mark in 10 ml syringes and autoclaved (120° C., 20 min). Before use, the columns are washed twice with 20 ml of PBS. To regulate the flow rate, a needle having a diameter of 0.8 mm is attached. During the subsequent washing with 10 ml of lymphocyte culture medium, the washing liquid is drawn off to the start of the column and the needle is then sealed with a rubber stopper. Up to $1 \times 10^8$ PBMC in 1 ml of medium are added to each column; to do this the rubber stopper is briefly pulled off in order to allow the cell-containing liquid to run in. A syringe stopper is then carefully attached in order to prevent the drying-out of the column and to avoid contamination during the following incubation for 45 min in an incubator (37° C., 5% $CO_2$). The T lymphocytes or NW-PBMC (nylon wool-purified PBMC) can be eluted by washing the column with 20 ml of lymphocyte culture medium with needle attached.

The determination of the immunoreactivity is carried out in a manner known per se according to methods which are described in the following references:

SAALMÜLLER, A., JONJIC, S., BÜHRING, H.-J., REDDEHASE, M. J. & KOSZINOWSKI, U. H. (1987). *Monoclonal antibodies reactive with swine lymphocytes. II. Detection of an antigen on resting T cells down-regulated after activation. J. Immunol.* 138, 1852–1857.

SAALMÜLLER, A. & MAURER, S. (1994). *Major histocompatibility antigen class II expressing porcine T lymphocytes are potent antigen-presenting cells in mixed leucocyte culture. Immunobiol.,* 190, 23–34.

SAALMÜLLER, A., HIRT, W., MAURER, S. & WEILAND, E. (1994). *Discrimination between two subsets of porcine $CD8^+$ cytolytic T lymphocytes by the expression of CD5 antigen. Immunology,* 81, 578–583.

PAULY, T., ELBERS, K., KÖNIG, M., LENGSFELD, T., SAALMÜLLER, A. & THIEL, H.-J (1995). *Classical Swine Fever Virus-specific cytolytic T lymphocytes and identification of a T cell epitope. J. Gen. Virol.,* 76, 3039–3049.

SUMMERFIELD, A., RZIHA, H.-J. & SAALMÜLLER, A. (1996). *Functional characterization of porcine $CD4^+CD8^+$ extrathymic T lymphocytes. Cell. Immunol.,* 168, 291–296.

PAULY, T., WEILAND, E., HIRT, W., DREYER-BUX, C., MAURER, S., SUMMERFIELD, A. & SAALMÜLLER, A. (1996). *Differentiation between MHC-restricted and non-MHC-restricted porcine cytolytic T lymphocytes. Immunology,* 88, 238–246.

For example, to this end the following measurement of the virus antigen-specific proliferation (proliferation assay) is described:

PBMC or cell populations isolated therefrom were inoculated into round-bottom microtitre plates at a cell count of $1 \times 10^5$ cells per microculture (200 µl/hollow) in a cell concentration of $1 \times 10^6$/ml in MEM alpha medium. Stimulation was carried out by addition of virus or peptides from the coding regions of the foot-and-mouth disease virus (FMDV) genome (specific activation). The virus amount added was indicated in MOI (multiplicity of infection), which corresponds to the number of infectious particles. The cells were then cultured in an incubator. After 5 days, 37 kBq (1 µCi) of $^3$H-thymidine/hollow, which was taken up in 20 µl of medium, were added and the culture was incubated for a further 18 h. The $^3$H-thymidine incorporation was then stopped by freezing the entire microtitre plate and the cells were lysed. With the aid of a cell harvester, the contents of the microtitre plate were aspirated onto filter mats. These were dried in a microwave oven (160 W, about 5 min). A solid scintillator plate was then fused onto the filter mat in the microwave oven (160 W, about 2 min). After cooling of the scintillator, the filter mat was sealed into a transparent sample bag and the radioactivity of the individual cultures was measured in disintegrations per minute (counts per minute, cpm) in a scintillation counter.

Determination of the IL-2 Content from the Cell Culture Supernatant of T Lymphocytes Specifically Activated by Virus Antigen (IL-2 Assay)

For semiquantitative determination of the interleukin-2 (IL-2) content of porcine leucocyte cultures, the murine, IL-2-dependent HT-2 cell line is used. This cell line grows only in the presence of IL-2, which can be of either murine, human or porcine origin. The proliferation of the HT-2 cell line is thus a measure of the IL-2 content in the cell culture supernatant, which in turn correlates with the IL-2 production of the respective cell population.

After activation of PBMC or cell populations isolated therefrom, 100 µl of cell-free supernatant from the respective hollows of the microtitre plate were removed after 5 days. Three parallel samples were combined and titrated in round-bottom microtitre plates in log2 steps (supernatant 1:1, 1:2, 1:4 and 1:8 in medium; in each case 100 µl/microculture). Finally, 100 µl of a cell suspension containing $4 \times 10^3$ HT-2 cells per hollow are added such that the final volume is 200 µl/hollow. To measure the proliferation of the HT-2 cells, triplicate cultures were prepared in each case. As a reference substance, human, recombinant IL-2 having a known number of international units (IU) was additionally taken and titrated over several steps. The growth of the HT-2 cells was quantified by determination of the DNA synthesis. To do this, $^3$H-thymidine (37 kBq/micro-culture) was added after incubation for 24 h and the cells were then incubated in an incubator for a further 18 h. The remainder of the method corresponds to that for the measurement of lymphocyte proliferation.

Measurement of the Cytolytic Activity of Virus Antigen-Specific Cytolytic T Lymphocytes Virus antigen-specific cytolytic T lymphocytes are formed by at least one weeks' co-culturing of PBMC of an infected animal or cell populations isolated therefrom ($2 \times 10^5$ cells/hollow) with autologous FMDV-infected (1–10 MOI) kidney epithelial cells. The virus antigen-specific activity of the cytolytic T lymphocytes (CTL) generated here was determined by means of $^{51}$chromium release tests. In these tests, the CTL was co-cultured for 4 to 8 hours either with autologous $^{51}$chromium-labelled FMDV-infected kidney epithelial cells or peptide-loaded kidney epithelial cells and the chromium released by the CTL activity was then determined in the supernatant of the respective cell cultures. Non-infected kidney epithelial cells were additionally included as controls for this experiment. The specific activity of the CTL is calculated by means of the following formula:

% specific lysis=$x$−spontaneous lysis/total incorporation−spontaneous lysis.

For the further analysis of CTL epitopes, recombinant vaccinia FMD viruses were also employed, the vaccinia viruses carrying subsequences of FMDV and expressing them in an infection.

The peptides were prepared in a manner known per se. For example, multiple peptide synthesis was carried out on a modified Tecan robot.

In this process, 30 mg each of the ADPV resin (loading 0.4 mmol/g) was weighed into the reaction vessels for the preparation of the hexapeptides. For the micro-synthesis of the other peptides, 5 mg each of the Rink amide MBHA resin (0.47 mmol/g) were used.

The sequences of the peptides to be prepared were then fed into the control computer of the synthesizer and the required Fmoc amino acids were weighed into the storage vessels. The amino acids were dissolved in 0.5 M HOBt in DMF to give a concentration of 0.5 M. Poorly soluble amino acids were treated in an ultrasonic bath for 5–10 min until a clear solution was present. The 2 M DIC solution required for activation was prepared using DCM/DMF (8:2). Piperidine, for the removal of the Fmoc protective group, is diluted to 40% in DMF and provided in the synthesizer with the DIC solution. The synthesis of the peptides took place by means of simple coupling and was carried out according to the following synthesis protocol:

1. Fmoc removal by 100 $\mu$l of 40% piperidine for 15 min.
2. Six washing cycles with 150 $\mu$l of DMF each and for 0.3 min.
3. Addition of 30 ml of the coupling reagent (2 M DIC in DMF) to the reaction vessels.
4. Addition of 60 $\mu$l of the activated Fmoc-amino acid (Fmoc-AA dissolved in 0.5 M HOBt/DMF).
5. Allowing this solution to stand for 60 min for coupling of the amino acid.
6. Three washing cycles with 150 ml DMF each, 0.6 min.

After the end of the synthesis, the resins were washed twice with ether (200 $\mu$l) and dried.

To remove the peptides prepared in the microsynthesis, modified reagent K (0.75 g of crystalline phenol, 0.25 ml of ethanedithiol, 0.5 ml of thioanisole) was employed. All other peptides have been removed using thioanisole/thiocresol (1:1) in TFA. In this case, the synthesis tips were removed from the synthesis block and the outlet openings sealed with liquid wax. Concentrated TFA in this case slowly dissolves the wax in the outlet opening and the cleavage solution, with the peptide already removed from the resin, can now drip into the PP tubes placed under the synthesis tips. The side-chain protective groups can furthermore be removed in the PP tubes. 150 $\mu$l of scavenger/TFA solution per tip were added here and the mixture was incubated at room temperature for 3 h. Approximately 1 ml of ether/heptane (1:1) was then added to the PP tubes using an 8-channel syringe and the temperature was adjusted to −20° C. for 2 h. The precipitate formed was centrifuged off (2,000 rpm, 5 min), the ether was decanted off and the pellet was resuspended twice with diethyl ether (1–2 ml) using ultrasound and centrifuged again. Finally, the precipitate was taken up in 1–1.5 ml of tert-butyl alcohol/water (4:1) and lyophilized.

Isolation of Sera and Determination of the Content of Specific Antibodies

Obtainment of Bovine and Porcine Sera

Undiluted blood was incubated at room temperature until it had clotted and the fibrin had deposited together with the blood cells. The serum in the supernatant was aliquoted and stored at −20° C.

Standard Peptide ELISA

The standard peptide ELISA (enzyme linked immunosorbent assay) for the detection of virus-specific antibodies in sera of infected or vaccinated animals was carried out as follows.

The ELISA plates (Nunc-Immuno Plate Maxisorb) were coated with peptides in concentrations of 0.5. 1 and 3 $\mu$g per hollow. The peptides were first dissolved in DMSO at a concentration of 10 mg/ml. The stock solution of 1 mg/ml in distilled water was then prepared from this. 100 $\mu$l of the peptide stock solution diluted in distilled water-were-then dried overnight at 37° C. After this, the plates were preincubated at 37° C. with 3% bovine serum albumin (BSA) in PBS for 2 h in order to prevent non-specific binding in the following incubation steps. The plates were washed three times with PBS-Tween after each incubation step, and five times before the addition of the substrate. Both the sera employed and the conjugates were diluted in 0.5% BSA in PBS.

The sera of infected or vaccinated cattle or pigs were used at a concentration of 1:100. 80 µl each of the serum dilution per hollow were employed and incubated at 37° C. for 1 h. After washing, either goat anti-bovine (dilution 1:2,500) or goat anti-pig (dilution 1:5,000) was added to the corresponding horseradish peroxidase-coupled conjugate. It was then incubated at 37° C. again for 1 h. After several washing steps, 60 µl of substrate/hollow were added to detect positive samples. The substrate used was orthophenylenediamine (OPD) dissolved in citrate buffer. The reaction of the substrate by the horseradish peroxidase in the form of a colour reaction took place at room temperature in the dark. It was stopped with 2 M sulphuric acid after about 20 min if the coloration of the positive control employed was sufficient. The colour intensity was measured at 492 nm in an ELISA measuring apparatus.

Biotin-streptavidin ELISA

Since porcine sera exhibit an extremely high non-specific reaction, it was attempted to increase the sensitivity of the measuring system by a modified ELISA. To this end, biotinylated peptides were used.

These biotinylated peptides were employed in the same concentration as the peptides in the standard peptide ELISA. Instead of distilled water, however, they were diluted with PBS/0.5% BSA. 100 µl/hollow of this solution were applied to streptavidin-coated microtitre plates, and 50 µl of serum were added corresponding to the concentrations of the standard peptide ELISA.

After incubation at room temperature for 1 h, washing three times with washing buffer and addition of 150 µl of horseradish peroxidase-labelled goat anti-bovine or goat anti-pig antisera per hollow (for dilution see standard peptide ELISA), the plate was incubated at room temperature for 1 h. It was washed again three times and 150 µl of azino-di-3-ethyl-benzothiazoline-sulphonate (ABTS) substrate solution per hollow were added. The extinction (optical density, OD) was measured at 405 nm in an ELISA measuring apparatus after 15 min and 1 h in each case.

Competition ELISA

The ELISAs carried out until now, the standard peptide and biotin-streptavidin ELISA, are used as a rule to detect linear B-cell epitopes. Frequently, however, the immunoglobulin molecules concerned do not recognize any linear epitopes, but conformational epitopes. This type of epitope can in certain circumstances be detected in the competition ELISA. To this end, ELISA plates (Nunc-Immuno Plate Maxisorb) were first coated overnight with 100 µl of a protein solution at a suitable concentration, which still showed a positive reaction in the standard peptide ELISA. The plates were then preincubated with PBS/3% BSA for 2 h corresponding to the standard peptide ELISA. Before the addition of the serum (concentration 1:1,000), this was preincubated in a microtitre plate for at least 1 h with 100 µg/ml of the peptides to be investigated. The procedure corresponding to the standard peptide ELISA was then followed.

Results

Identification of Linear B-Cell Epitopes

To identify linear B-cell epitopes of FMDV in cattle and pigs, 14mer and 15mer peptides, which were synthesized corresponding to the open reading frame of the FMDV genome, were investigated to see whether they are recognized by antibodies of sera of infected or vaccinated animals.

Investigation of Synthetic FMDV Peptides for Linear B-Cell Epitopes in the Pig

The peptides having the ID numbers 6, 8, 10, 12, 15, 16, 17, 18, 19, 20, 21, 23, 24, 25, 26, 27, 28, 29, 30, 31, 32, 34, 35, 36, 37, 38, 39, 43, 44, 45 of the sequence protocol were identified as B-cell epitopes of the pig.

Identification of Linear B-Cell Epitopes of FMDV in Cattle

The peptides having the ID numbers 12, 13, 14, 22, 33, 37, 40, 41, 42, 45, 46, 47, 48 of the sequence protocol were identified as linear B-cell epitopes of FMDV in cattle.

Identification of B-Cell Conformational Epitopes from the 3D Protein of FMDV

In carrying out a competition ELISA with recombinant 3D protein, 8 peptides were identified which are able to bind FMDV specific antibodies to the 3D protein from the serum. These are the peptides with the ID numbers 1, 2, 3, 4, 5, 7, 9, 11 of the sequence protocol.

Use of the Linear B-Cell Epitopes for Differentiating Between FMDV-Infected and Vaccinated Animals In this test, sera of animals infected and vaccinated with various serotypes of FMDV were investigated. The controls used were sera of non-infected animals and sera of animals which were infected with the bovine leukaemia virus (BLV).

It was seen that the peptide having the ID number 37 from the 2B region and ID number 48 from the 3B region of FMDV reacted positively with many sera of FMDV-infected or vaccinated animals. As a rule, it showed no reaction with sera of BLV-infected animals or negative sera.

It is further possible to ascertain that sera of FMDV strain $O_1K$-infected animals reacted with the greatest number of peptides in comparison with the other test groups. A difference between type O-infected and vaccinated animals is also detectible. In contrast to vaccinated animals which reacted especially with the peptide of ID number 37, 48 and the control peptide G1-32, the sera of infected animals additionally showed a distinct reactivity with the peptides of ID numbers 12, 13, 40, 42, 45, 47, 48.

BIBLIOGRAPHY

Beck E. and Strohmaier K. (1987) Subtyping of European foot-and-mouth disease virus strains by nucleotide sequence determination. J. Virol. 61: 1621–1629.

Collen T., DiMarchi R. and Doel T. R. (1991) A T cell epitope in VP1 of foot-and-mouth disease virus is immunodominant for vaccinated cattle. J. Immunol. 146: 749–755.

Glass E. J., and Spooner R. L. (1989) Requirement for MHC class II positive accessory cells in an antigen specific bovine T cell response. Res. Vet. Sci. 46: 196–201.

Glass E. J., Oliver R. A. and Spooner R. L. (1990) Variation in T cell responses to ovalbumin in cattle: evidence for Ir gene control. Animal Genetics 21: 15–28.

Glass E. J., Oliver R. A., Collen T., Doel T. R., DiMarchi R. and Spooner R. L. (1992) MHC class II restricted recognition of FMDV peptides by bovine T cells. Immunology 74: 594–9.

Hedger R. S. (1970) Observations on the carrier state and related antibody titres during an outbreak of foot-and-mouth disease. Journal of Hygiene 68: 53–60.

Rueckert R. R. (1990) Picornaviridae and their replication. In: Virology Sec. Ed. 507–548. (Fields B. N. et al.) Raven Press, New York.

Schwartz R. H. (1985) T-lymphocyte recognition of antigen in association with gene products of the major histocompatibility complex. Annu. Rev. Immunol. 3: 237–61.

Terpstra C. and van Maanen C. (1989) Protection and virus transmission of Dutch cattle following intranasal challenge with homologous and heterologous FMD virus strains 1–3 years after three consecutive annual vaccinations. Report of the 11th International Symposium of the world association of Veterinary Microbiologists, Immunologists and Specialists in Infectious Diseases, Perugia-Mantova, Italy, 2–6 October, p. 154. Esculapio, Bologna.

van Bekkum J. G. (1973) The carrier state in foot-and-mouth disease. In: Pollard M., ed. Proceedings of the 11th International Conference on FMD. New York: Gustav Stern Foundation Inc., 1973: 37–44.

What is claimed is:

1. A peptide consisting of a polypeptide sequence of SEQ ID NO. 45.

* * * * *

```
                              SEQUENCE LISTING

<160> NUMBER OF SEQ ID NOS: 48

<210> SEQ ID NO 1
<211> LENGTH: 15
<212> TYPE: PRT
<213> ORGANISM: Foot-and-mouth disease virus

<400> SEQUENCE: 1

Gly Arg Val His Val Met Arg Lys Thr Lys Leu Ala Pro Thr Val
1               5                   10                  15

<210> SEQ ID NO 2
<211> LENGTH: 15
<212> TYPE: PRT
<213> ORGANISM: Foot-and-mouth disease virus

<400> SEQUENCE: 2

Met Arg Lys Thr Lys Leu Ala Pro Thr Val Ala His Gly Val Phe
1               5                   10                  15

<210> SEQ ID NO 3
<211> LENGTH: 15
<212> TYPE: PRT
<213> ORGANISM: Foot-and-mouth disease virus

<400> SEQUENCE: 3

Leu Ala Pro Thr Val Ala His Gly Val Phe Asn Pro Glu Phe Gly
1               5                   10                  15

<210> SEQ ID NO 4
<211> LENGTH: 15
<212> TYPE: PRT
<213> ORGANISM: Foot-and-mouth disease virus

<400> SEQUENCE: 4

Arg Cys Ala Ala Asp Tyr Ala Ser Arg Leu His Ser Val Leu Gly
1               5                   10                  15

<210> SEQ ID NO 5
<211> LENGTH: 15
<212> TYPE: PRT
<213> ORGANISM: Foot-and-mouth disease virus

<400> SEQUENCE: 5

Asn Gly Thr Val Gly Pro Glu Val Glu Ala Ala Leu Lys Leu Met
1               5                   10                  15

<210> SEQ ID NO 6
<211> LENGTH: 15
<212> TYPE: PRT
<213> ORGANISM: Foot-and-mouth disease virus

<400> SEQUENCE: 6
```

-continued

Glu Lys Arg Glu Tyr Lys Phe Val Cys Gln Thr Phe Leu Lys Asp
1               5                   10                  15

<210> SEQ ID NO 7
<211> LENGTH: 15
<212> TYPE: PRT
<213> ORGANISM: Foot-and-mouth disease virus

<400> SEQUENCE: 7

Ala Gln Met His Ser Asn Asn Gly Pro Gln Ile Gly Ser Ala Val
1               5                   10                  15

<210> SEQ ID NO 8
<211> LENGTH: 15
<212> TYPE: PRT
<213> ORGANISM: Foot-and-mouth disease virus

<400> SEQUENCE: 8

Ile Gly Ser Ala Val Gly Cys Asn Pro Asp Val Asp Trp Gln Arg
1               5                   10                  15

<210> SEQ ID NO 9
<211> LENGTH: 15
<212> TYPE: PRT
<213> ORGANISM: Foot-and-mouth disease virus

<400> SEQUENCE: 9

Val Trp Asp Val Asp Tyr Ser Ala Phe Asp Ala Asn His Cys Ser
1               5                   10                  15

<210> SEQ ID NO 10
<211> LENGTH: 15
<212> TYPE: PRT
<213> ORGANISM: Foot-and-mouth disease virus

<400> SEQUENCE: 10

Glu Asn Lys Arg Ile Thr Val Gly Gly Gly Met Pro Ser Gly Cys
1               5                   10                  15

<210> SEQ ID NO 11
<211> LENGTH: 15
<212> TYPE: PRT
<213> ORGANISM: Foot-and-mouth disease virus

<400> SEQUENCE: 11

His Phe Lys Ser Leu Gly Gln Thr Ile Thr Pro Ala Asp Lys Ser
1               5                   10                  15

<210> SEQ ID NO 12
<211> LENGTH: 15
<212> TYPE: PRT
<213> ORGANISM: Foot-and-mouth disease virus

<400> SEQUENCE: 12

Leu Lys Ala Arg Asp Ile Asn Asp Ile Phe Ala Ile Leu Lys Asn
1               5                   10                  15

<210> SEQ ID NO 13
<211> LENGTH: 15
<212> TYPE: PRT
<213> ORGANISM: Foot-and-mouth disease virus

<400> SEQUENCE: 13

Ser Glu Glu Lys Phe Val Thr Met Thr Asp Leu Val Pro Gly Ile
1               5                   10                  15

```
<210> SEQ ID NO 14
<211> LENGTH: 15
<212> TYPE: PRT
<213> ORGANISM: Foot-and-mouth disease virus

<400> SEQUENCE: 14

Val Thr Met Thr Asp Leu Val Pro Gly Ile Leu Glu Lys Gln Arg
1               5                   10                  15

<210> SEQ ID NO 15
<211> LENGTH: 15
<212> TYPE: PRT
<213> ORGANISM: Foot-and-mouth disease virus

<400> SEQUENCE: 15

Thr Gly Phe Ile Pro Pro Met Ala Ser Leu Glu Asp Lys Gly Lys
1               5                   10                  15

<210> SEQ ID NO 16
<211> LENGTH: 15
<212> TYPE: PRT
<213> ORGANISM: Foot-and-mouth disease virus

<400> SEQUENCE: 16

Pro Asn Thr Ser Gly Leu Glu Thr Arg Val Val Gln Ala Glu Arg
1               5                   10                  15

<210> SEQ ID NO 17
<211> LENGTH: 15
<212> TYPE: PRT
<213> ORGANISM: Foot-and-mouth disease virus

<400> SEQUENCE: 17

Glu Leu Tyr Gln Leu Thr Leu Phe Pro His Gln Phe Ile Asn Pro
1               5                   10                  15

<210> SEQ ID NO 18
<211> LENGTH: 15
<212> TYPE: PRT
<213> ORGANISM: Foot-and-mouth disease virus

<400> SEQUENCE: 18

Val Met Val Val Ala Pro Leu Thr Val Asn Thr Glu Gly Ala Pro
1               5                   10                  15

<210> SEQ ID NO 19
<211> LENGTH: 15
<212> TYPE: PRT
<213> ORGANISM: Foot-and-mouth disease virus

<400> SEQUENCE: 19

Leu Ala Gly Leu Ala Gln Tyr Tyr Thr Gln Tyr Ser Gly Thr Ile
1               5                   10                  15

<210> SEQ ID NO 20
<211> LENGTH: 15
<212> TYPE: PRT
<213> ORGANISM: Foot-and-mouth disease virus

<400> SEQUENCE: 20

Glu Thr Thr Asn Val Gln Gly Trp Val Cys Leu Phe Gln Ile Thr
1               5                   10                  15
```

<210> SEQ ID NO 21
<211> LENGTH: 15
<212> TYPE: PRT
<213> ORGANISM: Foot-and-mouth disease virus

<400> SEQUENCE: 21

Gln Gly Trp Val Cys Leu Phe Gln Ile Thr His Gly Lys Ala Asp
1               5                   10                  15

<210> SEQ ID NO 22
<211> LENGTH: 15
<212> TYPE: PRT
<213> ORGANISM: Foot-and-mouth disease virus

<400> SEQUENCE: 22

Tyr Asn Arg Asn Ala Val Pro Asn Leu Arg Gly Asp Leu Gln Val
1               5                   10                  15

<210> SEQ ID NO 23
<211> LENGTH: 15
<212> TYPE: PRT
<213> ORGANISM: Foot-and-mouth disease virus

<400> SEQUENCE: 23

Glu Ile Lys Ala Leu Phe Leu Ser Arg Thr Thr Gly Lys Met Glu
1               5                   10                  15

<210> SEQ ID NO 24
<211> LENGTH: 15
<212> TYPE: PRT
<213> ORGANISM: Foot-and-mouth disease virus

<400> SEQUENCE: 24

Cys Trp Leu Asn Ala Ile Leu Gln Leu Phe Arg Tyr Val Glu Glu
1               5                   10                  15

<210> SEQ ID NO 25
<211> LENGTH: 15
<212> TYPE: PRT
<213> ORGANISM: Foot-and-mouth disease virus

<400> SEQUENCE: 25

Arg Tyr Val Glu Glu Pro Phe Phe Asp Trp Val Tyr Ser Ser Pro
1               5                   10                  15

<210> SEQ ID NO 26
<211> LENGTH: 15
<212> TYPE: PRT
<213> ORGANISM: Foot-and-mouth disease virus

<400> SEQUENCE: 26

Glu Ala Ile Lys Gln Leu Glu Asp Leu Thr Gly Leu Glu Leu His
1               5                   10                  15

<210> SEQ ID NO 27
<211> LENGTH: 15
<212> TYPE: PRT
<213> ORGANISM: Foot-and-mouth disease virus

<400> SEQUENCE: 27

Asn Ile Lys His Leu Leu His Thr Gly Ile Gly Thr Ala Ser Arg
1               5                   10                  15

<210> SEQ ID NO 28
<211> LENGTH: 15

```
<212> TYPE: PRT
<213> ORGANISM: Foot-and-mouth disease virus

<400> SEQUENCE: 28

Ala Ile Asp Asp Glu Asp Phe Tyr Pro Trp Thr Pro Asp Pro Ser
1               5                   10                  15

<210> SEQ ID NO 29
<211> LENGTH: 15
<212> TYPE: PRT
<213> ORGANISM: Foot-and-mouth disease virus

<400> SEQUENCE: 29

Thr Pro Asp Pro Ser Asp Val Leu Val Phe Val Pro Tyr Asp Gln
1               5                   10                  15

<210> SEQ ID NO 30
<211> LENGTH: 15
<212> TYPE: PRT
<213> ORGANISM: Foot-and-mouth disease virus

<400> SEQUENCE: 30

Thr Asp Leu Gln Lys Met Val Met Gly Asn Thr Lys Pro Val Glu
1               5                   10                  15

<210> SEQ ID NO 31
<211> LENGTH: 15
<212> TYPE: PRT
<213> ORGANISM: Foot-and-mouth disease virus

<400> SEQUENCE: 31

Met Leu Ser Asp Ala Ala Leu Met Val Leu His Arg Gly Asn Arg
1               5                   10                  15

<210> SEQ ID NO 32
<211> LENGTH: 15
<212> TYPE: PRT
<213> ORGANISM: Foot-and-mouth disease virus

<400> SEQUENCE: 32

Leu Leu Lys Met Lys Ala His Ile Asp Pro Glu Pro His His Glu
1               5                   10                  15

<210> SEQ ID NO 33
<211> LENGTH: 15
<212> TYPE: PRT
<213> ORGANISM: Foot-and-mouth disease virus

<400> SEQUENCE: 33

Pro Phe Phe Phe Ser Asp Val Arg Ser Asn Phe Ser Lys Leu Val
1               5                   10                  15

<210> SEQ ID NO 34
<211> LENGTH: 14
<212> TYPE: PRT
<213> ORGANISM: Foot-and-mouth disease virus

<400> SEQUENCE: 34

Ala Pro Val Leu Leu Ala Gly Leu Val Lys Val Ala Ser Ser
1               5                   10

<210> SEQ ID NO 35
<211> LENGTH: 14
<212> TYPE: PRT
<213> ORGANISM: Foot-and-mouth disease virus
```

```
<400> SEQUENCE: 35

Ala Gly Leu Val Lys Val Ala Ser Ser Phe Phe Arg Ser Thr
1               5                  10

<210> SEQ ID NO 36
<211> LENGTH: 14
<212> TYPE: PRT
<213> ORGANISM: Foot-and-mouth disease virus

<400> SEQUENCE: 36

Val Ala Ser Ser Phe Phe Arg Ser Thr Pro Glu Asp Leu Glu
1               5                  10

<210> SEQ ID NO 37
<211> LENGTH: 14
<212> TYPE: PRT
<213> ORGANISM: Foot-and-mouth disease virus

<400> SEQUENCE: 37

Phe Phe Arg Ser Thr Pro Glu Asp Leu Glu Arg Ala Glu Lys
1               5                  10

<210> SEQ ID NO 38
<211> LENGTH: 14
<212> TYPE: PRT
<213> ORGANISM: Foot-and-mouth disease virus

<400> SEQUENCE: 38

Ile Ser Ile Pro Ser Gln Lys Ser Val Leu Tyr Phe Leu Ile
1               5                  10

<210> SEQ ID NO 39
<211> LENGTH: 14
<212> TYPE: PRT
<213> ORGANISM: Foot-and-mouth disease virus

<400> SEQUENCE: 39

Lys Arg Gln Lys Met Val Asp Asp Ala Val Asn Glu Tyr Ile
1               5                  10

<210> SEQ ID NO 40
<211> LENGTH: 14
<212> TYPE: PRT
<213> ORGANISM: Foot-and-mouth disease virus

<400> SEQUENCE: 40

Asn Glu Tyr Ile Glu Lys Ala Asn Ile Thr Thr Asp Asp Lys
1               5                  10

<210> SEQ ID NO 41
<211> LENGTH: 14
<212> TYPE: PRT
<213> ORGANISM: Foot-and-mouth disease virus

<400> SEQUENCE: 41

Thr Asp Asp Lys Thr Leu Asp Glu Ala Glu Lys Ser Pro Leu
1               5                  10

<210> SEQ ID NO 42
<211> LENGTH: 14
<212> TYPE: PRT
<213> ORGANISM: Foot-and-mouth disease virus

<400> SEQUENCE: 42
```

```
Thr Val Gly Phe Arg Glu Arg Thr Leu Pro Gly Gln Lys Ala
1               5                   10
```

<210> SEQ ID NO 43
<211> LENGTH: 14
<212> TYPE: PRT
<213> ORGANISM: Foot-and-mouth disease virus

<400> SEQUENCE: 43

```
Asp Asp Val Asn Ser Glu Pro Ala Gln Pro Val Glu Glu Gln
1               5                   10
```

<210> SEQ ID NO 44
<211> LENGTH: 14
<212> TYPE: PRT
<213> ORGANISM: Foot-and-mouth disease virus

<400> SEQUENCE: 44

```
Asn Thr Gly Ser Ile Ile Asn Asn Tyr Tyr Met Gln Gln Tyr
1               5                   10
```

<210> SEQ ID NO 45
<211> LENGTH: 14
<212> TYPE: PRT
<213> ORGANISM: Foot-and-mouth disease virus

<400> SEQUENCE: 45

```
Gly Pro Tyr Ala Gly Pro Leu Glu Arg Gln Lys Pro Leu Lys
1               5                   10
```

<210> SEQ ID NO 46
<211> LENGTH: 14
<212> TYPE: PRT
<213> ORGANISM: Foot-and-mouth disease virus

<400> SEQUENCE: 46

```
Pro Leu Glu Arg Gln Lys Pro Leu Lys Val Arg Ala Lys Leu
1               5                   10
```

<210> SEQ ID NO 47
<211> LENGTH: 14
<212> TYPE: PRT
<213> ORGANISM: Foot-and-mouth disease virus

<400> SEQUENCE: 47

```
Gly Pro Tyr Ala Gly Pro Met Glu Arg Gln Lys Pro Leu Lys
1               5                   10
```

<210> SEQ ID NO 48
<211> LENGTH: 14
<212> TYPE: PRT
<213> ORGANISM: Foot-and-mouth disease virus

<400> SEQUENCE: 48

```
Pro Met Glu Arg Gln Lys Pro Leu Lys Val Lys Ala Lys Ala
1               5                   10
```